US011504023B2

(12) United States Patent
Wolfson et al.

(10) Patent No.: US 11,504,023 B2
(45) Date of Patent: Nov. 22, 2022

(54) SPARSE CALIBRATION OF MAGNETIC FIELD CREATED BY COILS IN METAL-RICH ENVIRONMENT

(71) Applicant: BIOSENSE WEBSTER (ISRAEL) LTD., Yokneam (IL)

(72) Inventors: Helen Wolfson, Haifa (IL); Avram Dan Montag, Haifa (IL); Meir Bar-Tal, Haifa (IL); Yoav Pinsky, Bet Keshet (IL); Noam Racheli, Hadera (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 194 days.

(21) Appl. No.: 16/716,278

(22) Filed: Dec. 16, 2019

(65) Prior Publication Data
US 2021/0177298 A1 Jun. 17, 2021

(51) Int. Cl.
*A61B 5/00* (2006.01)
*A61B 5/06* (2006.01)
*G01B 7/004* (2006.01)

(52) U.S. Cl.
CPC ............ *A61B 5/062* (2013.01); *G01B 7/004* (2013.01); *A61B 2560/0223* (2013.01); *A61B 2562/0223* (2013.01)

(58) Field of Classification Search
None
See application file for complete search history.

(56) References Cited

U.S. PATENT DOCUMENTS

| 6,335,617 | B1* | 1/2002 | Osadchy | A61B 5/06 324/202 |
|---|---|---|---|---|
| 6,836,745 | B2 | 12/2004 | Seiler et al. | |
| 7,353,125 | B2 | 4/2008 | Nieminen et al. | |
| 2003/0176799 | A1 | 9/2003 | Beatty et al. | |
| 2004/0021465 | A1 | 2/2004 | Hollis | |
| 2007/0038410 | A1 | 2/2007 | Tunay | |

(Continued)

FOREIGN PATENT DOCUMENTS

EP 1776923 4/2007

OTHER PUBLICATIONS

International Search Report dated Mar. 17, 2021 from corresponding PCT Patent Application No. PCT/IB2020/060834.

*Primary Examiner* — Joel F Brutus
(74) *Attorney, Agent, or Firm* — Frost Brown Todd LLC

(57) ABSTRACT

A calibration method includes receiving magnetic field values, which are generated by a plurality of real magnetic transmitters and are measured at multiple positions on a grid in a region containing a magnetic field perturbing element. Approximate locations of the real magnetic transmitters are received. Using the approximate locations, a respective plurality of imaginary magnetic sources is characterized inside the field perturbing element. Using the measured magnetic field values, the approximate locations, and the characterized imaginary sources, there are iteratively calculated (i) actual locations of the real and imaginary magnetic sources in the region, and (ii) modeled magnetic field values that would result from the real and imaginary magnetic sources at the actual locations. Using the calculated locations, and the modeled magnetic field values at the multiple positions on the grid, a magnetic field calibration function is derived for the region.

14 Claims, 5 Drawing Sheets

(56) References Cited

U.S. PATENT DOCUMENTS

| | | |
|---|---|---|
| 2010/0082280 A1 | 4/2010 | Schneider |
| 2012/0165656 A1 | 6/2012 | Montag et al. |
| 2016/0011288 A1 | 1/2016 | Overweg et al. |

* cited by examiner

SPARSE CALIBRATION OF MAGNETIC FIELD CREATED BY COILS IN METAL-RICH ENVIRONMENT

FIELD OF THE INVENTION

The present invention relates generally to sensing a position of an object placed within a living body, and specifically to compensation for magnetic disturbances affecting a sensor of the position.

BACKGROUND OF THE INVENTION

Techniques to assist the tracking of an invasive probe inside a cavity of an organ using magnetic fields have been previously proposed in the patent literature. For example, U.S. Patent Application Publication 2012/0165656, issued as U.S. Pat. No. 8,812,079 on Aug. 19, 2014, describes a method, consisting of generating, using a plurality of magnetic transmitters, a magnetic field in a region and introducing a field perturbing element into the region. The method includes characterizing multiple images of each magnetic transmitter in the field perturbing element, and calculating a reaction magnetic field in the region based on the characterized images. The method further includes positioning a probe in the region and measuring a perturbed magnetic field at the probe, and determining a location of the probe in response to the measured perturbed magnetic field and the calculated reaction magnetic field.

U.S. Patent Application Publication 2016/0011288, issued as U.S. Pat. No. 10,324,148 on Jun. 18, 2019, describes a medical apparatus comprising: a magnetic resonance imaging system; magnetic compensation coils for compensating for magnetic inhomogeneities within the imaging zone; a gantry operable for rotating about the imaging zone; a position sensor for measuring the angular position and the angular velocity of the gantry; at least one magnetic field distorting component in the gantry, a memory that stores machine executable instructions and field correction data. The instructions cause a processor to: receive the position and angular velocity data from the position sensor; determine coil control commands for controlling the magnetic compensation coils using the field correction data, the position data and the angular velocity data; control the magnetic compensation coils to compensate for magnetic inhomogeneities within the imaging zone using the coil control commands; and acquire the magnetic resonance data.

SUMMARY OF THE INVENTION

An embodiment of the present invention provides a calibration method including receiving magnetic field values, which are generated by a plurality of real magnetic transmitters and are measured at multiple positions on a grid in a region containing a magnetic field perturbing element. Approximate locations of the real magnetic transmitters are received. Using the approximate locations, a respective plurality of imaginary magnetic sources is characterized inside the field perturbing element. Using the measured magnetic field values, the approximate locations, and the characterized imaginary sources, there are iteratively calculated (i) actual locations of the real and imaginary magnetic sources in the region, and (ii) modeled magnetic field values that would result from the real and imaginary magnetic sources at the actual locations. Using the calculated locations, and the modeled magnetic field values at the multiple positions on the grid, a magnetic field calibration function is derived for the region.

In some embodiments, receiving the magnetic field values includes positioning a probe in the region and measuring the generated magnetic field at the probe over the multiple positions.

In some embodiments, characterizing the imaginary magnetic sources includes estimating a location of each of the imaginary magnetic sources inside the perturbing element.

In an embodiment, the magnetic field calibration function is provided as a three-dimensional array of values over a calibrated grid of positions, which is denser than the grid used for measuring the magnetic field values.

In another embodiment, deriving the magnetic field calibration function includes modeling the magnetic fields generated by the real and imaginary magnetic sources as linear combinations of spherical harmonic functions, and evaluating the modeled magnetic fields at the actual locations.

There is additionally provided, in accordance with another embodiment of the present invention, an apparatus, including a memory and a processor. The memory is configured for storing magnetic field values, which are generated by a plurality of real magnetic transmitters and are measured at multiple positions on a grid in a region containing a magnetic field perturbing element, and for storing approximate locations of the real magnetic transmitters. The processor is configured to (a) using the approximate locations of the real magnetic transmitters, characterize a respective plurality of imaginary magnetic sources inside the field perturbing element, (b) using the measured magnetic field values, the approximate locations, and the characterized imaginary sources, iteratively calculate (i) actual locations of the real and imaginary magnetic sources in the region and (ii) modeled magnetic field values that would result from the real and imaginary magnetic sources at the actual locations, and (c) using the calculated locations, and the modeled magnetic field values at the multiple positions on the grid, derive a magnetic field calibration function for the region.

The present invention will be more fully understood from the following detailed description of the embodiments thereof, taken together with the drawings in which:

DETAILED DESCRIPTION OF EMBODIMENTS

Overview

Figure 1:
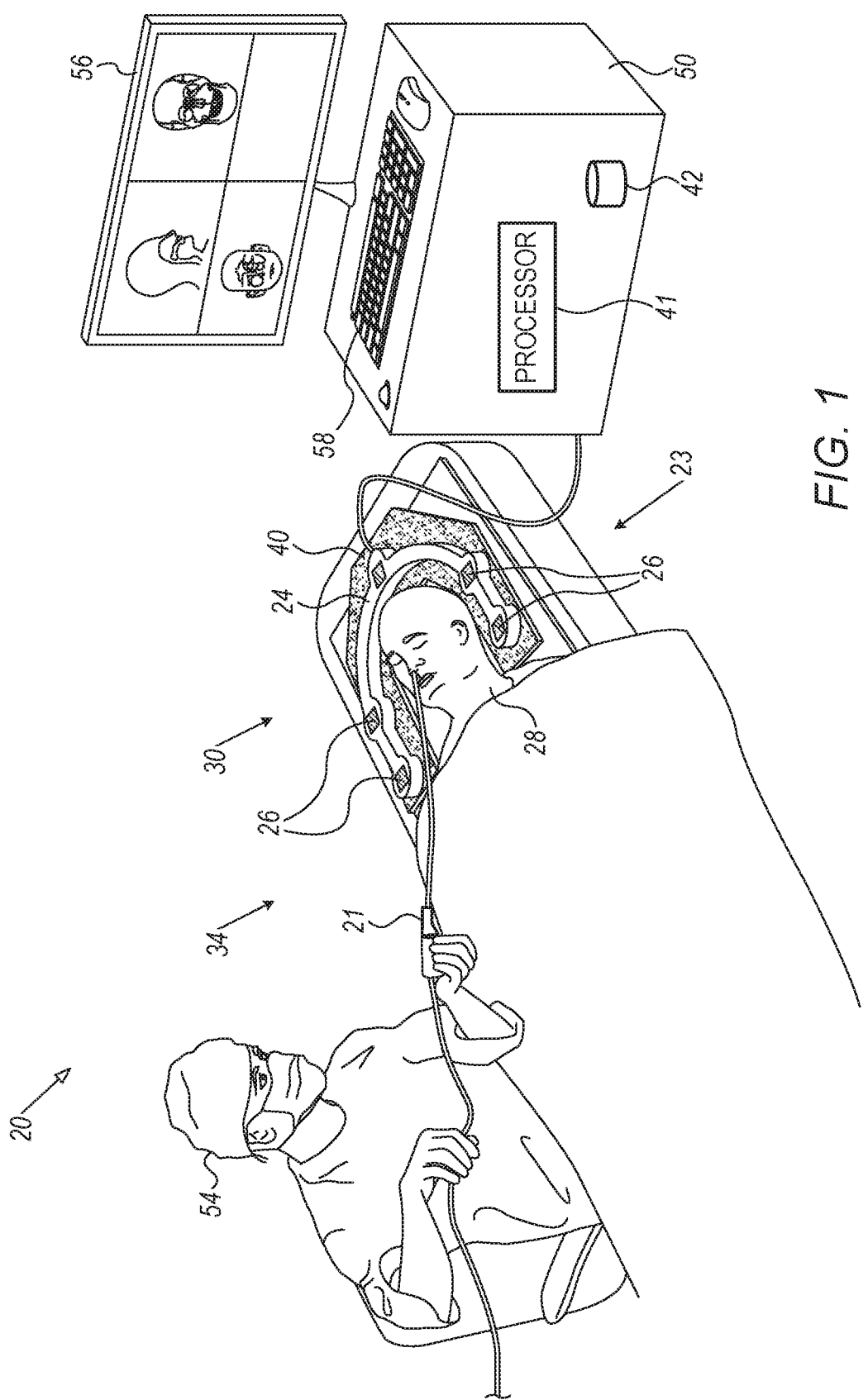
FIG. 1 is a schematic, pictorial illustration of an ear-nose-throat (ENT) system comprising a magnetic position-tracking sub-system, in accordance with an embodiment of the present invention.

Tracking a probe in an organ of a patient using a magnetic position senor fitted at a distal end of the probe requires calibration of the external magnetic tracking system. In some cases, the magnetic field generated by the system is perturbed by a presence of a magnetic-field-perturbing metal-rich element, such as a piece of equipment in the vicinity of the system's magnetic field generators. The perturbation complicates the calibration, as it requires the use of a dense grid of calibrated locations in space. Typically, such a complicated calibration may require a day-long measurement of tens of thousands of magnetic field values in 3D space using a calibration probe.

Embodiments of the present invention provide a fast calibration method of a perturbed magnetic field in the vicinity of static metal-rich elements, such as a metal base that provides mechanical support to a set of coil magnetic field generators (also called hereinafter "real magnetic sources," or "coil transmitters") of a position tracking system.

To take the presence of the perturbing element, e.g., a metal base for the coils, into account, embodiments of the present invention provide a calibration model which assumes that each coil transmitter generates eddy currents in the perturbing element. These eddy currents can be modeled as one or more image (or imaginary) magnetic sources. The calibration model further assumes that each imaginary magnetic source generates a respective reaction field which on the basis of linear superposition causes the perturbation in the magnetic field.

The disclosed fast calibration method includes (a) receiving magnetic field values, which are generated by a plurality of real magnetic transmitters and are measured at multiple positions on a grid in a region containing a magnetic field perturbing element, (b) receiving approximate locations of the real magnetic transmitters, (c) using the approximate locations, characterizing a respective plurality of imaginary magnetic sources inside the field perturbing element, (d) using the measured magnetic field values, the approximate locations, and the characterized imaginary sources, iteratively calculating (i) actual locations of the real and imaginary magnetic sources in the region and (ii) modeled magnetic field values that would result from the real and imaginary magnetic sources at the actual locations, (e) and, using the calculated locations, and the modeled magnetic field values at the multiple positions on the grid, deriving a magnetic field calibration function for the region.

In some embodiments, each imaginary magnetic source is characterized as a combination of magnetic multipoles, i.e., dipoles, quadrupoles and/or higher-order multipoles. Characteristics of each imaginary magnetic source are also dependent, inter alia, on the real transmitter field generating the imaginary magnetic source. The calibration model calculates the reaction field from each of the multipolar imaginary magnetic sources by assuming that the field can be represented by a spherical harmonic expansion according to characteristics of the imaginary magnetic source. Spherical harmonics are especially convenient for this application, but other expansions, such as wavelets, would also be valid.

The actual locations of the real coil transmitters and the modeled locations of the respective imaginary magnetic sources are left as parameters to be solved by using an iterative calculation. The disclosed method thus includes adjusting the prespecified locations of the real coil transmitters, which may be inaccurate due to, for example, mechanical unrepeatability in producing a transmitter base assembly, and may therefore vary from system to system.

In an embodiment, a position-tracking system includes five triaxial magnetic transmitters, totaling fifteen actual coil transmitters, since each triaxial transmitter includes three mutually orthogonal coils. Each of the fifteen actual coil transmitters generates an imaginary coil transmitter in a metal base of a location pad of the position tracking system. Applying the calibration measurement values, and assuming that the actual and imaginary transmitter fields are given by a spherical harmonics model, the calibration provides effective positions of the actual transmitters and of the imaginary transmitters, and these positions are then used to find the magnetic field at any point in the working volume. Using a sparse grid for the calibration process requires fewer measured data points, of at least a factor of ten (×10), over the region than a previous calibration process. For this system, the disclosed technique shortens the typical duration of the calibration procedure from about a day to about an hour.

In an embodiment, the processor is configured to provide the magnetic field calibration function as a three-dimensional array of values over a calibrated grid of positions that is denser than the sparse grid used in the measurement.

Typically, the processor is programmed in software containing a particular algorithm that enables the processor to conduct each of the processor-related steps and functions outlined above.

Once the system has been calibrated, the processor is able to track a location of a medical probe in the magnetically perturbed region with high accuracy during a medical session.

System Description

FIG. 1 is a schematic, pictorial illustration of an ear-nose-throat (ENT) system 20 comprising a magnetic position-tracking sub-system 23, in accordance with an embodiment of the present invention. In the following description, an ENT tool 21 medical procedure inside the head of a patient 28, tool 21 comprises one or more magnetic sensors 34, typically single-axis coils or a triple-axis coils, that are tracked during the procedure by magnetic position-tracking sub-system 23.

For the tracking to be effective in system 20, frames of reference of a CT (computerized tomography) image of patient and of magnetic position-tracking sub-system 23 are registered. Both prior to, and during, the medical procedure, a magnetic tracking system, comprised of magnetic radiator assembly 24, is positioned beneath the patient's head.

To use a magnetic field transmitting system, such as described herein, magnetic radiator assembly 24 has to be mounted on a metal base 40. (Metal base 40 shields the transmitters from interfering metal that may be present in a bed or chair where patient 28 lies or is seated.) However, the transmitters and the base (which by itself introduces perturbation to the magnetic field) must be calibrated.

Assembly 24 comprises five magnetic field tri-coil transmitters 26 which are fixed in position and which transmit alternating magnetic fields into a region 30 wherein the head of patient 28 is located. Potentials generated in response to the magnetic fields by sensor 34 in region 30 enable the measurement of its position and its direction in the magnetic tracking system's frame of reference. The position can be measured in three linear dimensions (3D), while the direction of the distal end of tool 21 can be determined using one of the coils of sensor 34, whose axis is aligned with a longitudinal axis of the distal end.

By way of example, the five coil transmitter assemblies 26 of assembly 24 are arranged in an approximately horseshoe shape around the head of patient 28. However, alternate configurations for the coil transmitters of assembly 24 may be used, and all such configurations are assumed to be comprised within the scope of the present invention. Each of coil transmitters 26 comprises three mutually orthogonal coils that generate magnetic fields. Thus, system 20 has a total of fifteen (15) transmitter coils.

Prior to the procedure, the registration of the frames of reference of the magnetic tracking system with the CT image may be performed by positioning a magnetic sensor at known positions of the image, such as the top of the patient's head.

Elements of system 20, including coil transmitters 26 and sensors 34, are under overall control of a system processor 41. Processor 41 may be mounted in a console 50, which comprises operating controls 58 that typically include a keypad and/or a pointing device such as a mouse or trackball. Console 50 connects to the coil transmitters 26 and to sensor 34 wirelessly and/or via one or more cables. A physician 54 uses operating controls 58 to interact with the processor while performing the ENT procedure using system 20. While performing the procedure, the processor may present results of the procedure on a screen 56.

System 20 further comprises a memory 42. Processor 41 uses software stored in memory 42 to operate system 20. The software may be downloaded to processor 41 in electronic form, over a network, for example, or it may, alternatively or additionally, be provided and/or stored on non-transitory tangible media, such as magnetic, optical, or electronic memory. In particular, processor 41 runs a dedicated algorithm as disclosed herein, including in FIG. 6, which enables processor 41 to perform the disclosed steps, as further described below.

In some embodiments, memory 42 is also used for storing measured magnetic-field values and approximate locations of coil transmitter 36 as part of the disclosed calibration schemes, as will be explained below.

Sparse Calibration of Magnetic Field Created by Coils in Metal-Rich Environment

Figure 2:
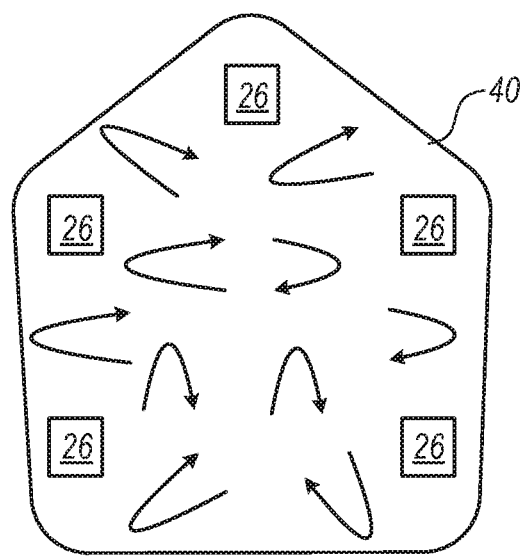
FIG. 2 is a schematic, pictorial front view of the magnetic radiator assembly mounted on a metal base of FIG. 1, in accordance with an embodiment of the present invention.

FIG. 2 is a front view of the magnetic radiator assembly 24 mounted on a metal base 40 of FIG. 1, in accordance with an embodiment of the present invention. Also seen are eddy currents that are generated in metal base 40 by coil transmitters 26, and which cause a perturbation to the magnetic field generated by coil transmitters 26.

Figure 3:
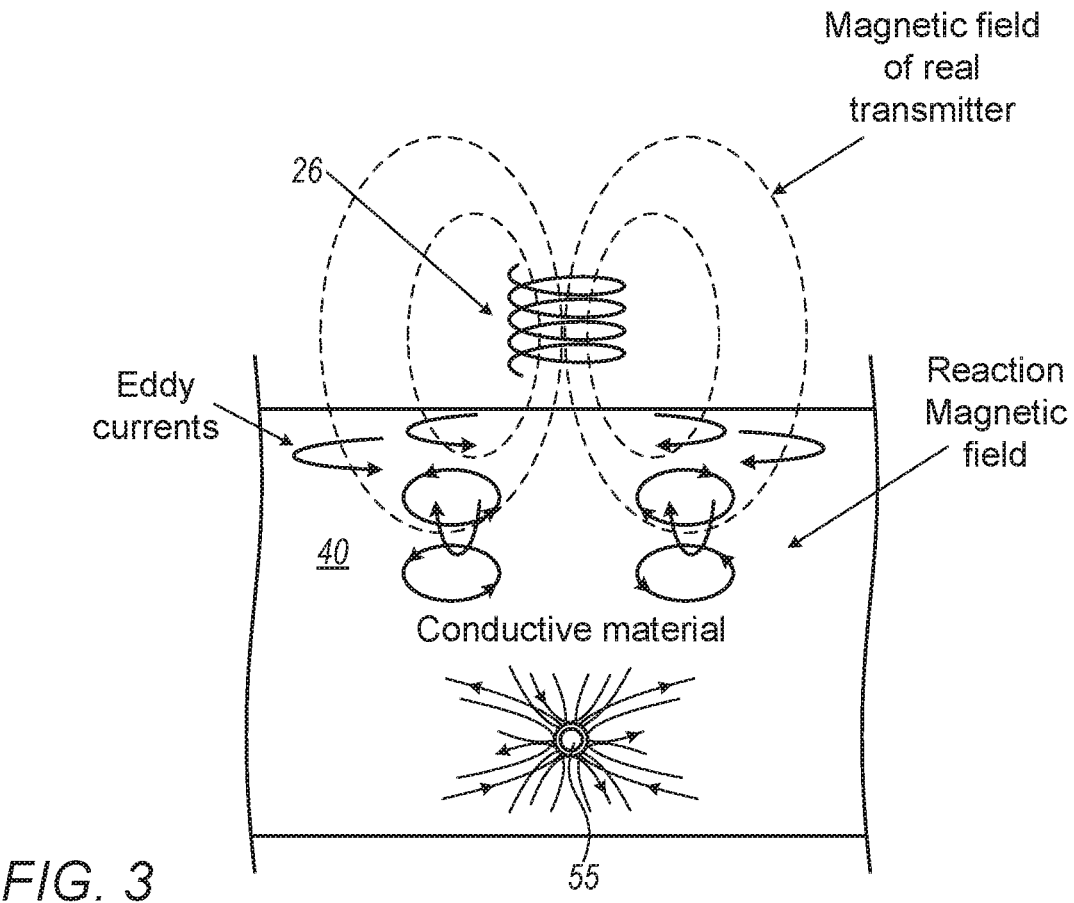
FIG. 3 is schematic, pictorial illustration of a real magnetic source and a respective imaginary magnetic source in the metal base of FIG. 2, in accordance with an embodiment of the present invention.

FIG. 3 is schematic, pictorial illustration of a real magnetic source 26 (e.g., coil transmitter 26) and a respective imaginary magnetic source 55 in metal base 40 of FIG. 2, in accordance with another embodiment of the present invention. An oscillating magnetic field generated by coil 26 induces eddy currents in metal base 40. The eddy currents generate a reaction magnetic field, which is modeled by assuming a single imaginary source 55. For the calibration, the method uses the sparsely measured total magnetic field to iteratively find the exact actual locations of coil 26 and modeled locations of imaginary source 55, so as to have a self-consistent calibration function.

The disclosed calibration model assumes that a real source 26 and an imaginary source 55 can both be described as a linear combination of spherical harmonics functions that generate a magnetic field given by:

$$B(r, \theta, \phi) = \frac{1}{r^3} \sum_{l,m} C_{l,m} Y_{l,m}(\theta, \phi) \qquad \text{Eq. 1}$$

For an array of N real sources 26, the model calculates 2N different $B(r,\theta,\phi)$ functions (including one for each imaginary sources), where in FIG. 2, N=5. In practice, each real source 26 is a triaxial coil, with each coil transmitting a magnetic field that oscillates at a unique frequency. Typically, for each frequency, there are 15 spherical harmonic coefficients that are unknown, which corresponds to taking 15 $Y_{l,m}(\theta, \phi)$ terms in Eq. 1 to describe a magnetic field at a given frequency, with l running from 1 to 3 and m running from 0 to l. Add to that are 3 location coordinates unknowns per each triaxial coil. The imaginary source has a same number of unknowns as the real source. There are therefore 48 unknowns to find for each triaxial coil (i.e., 45 spherical harmonics coefficients+3 location coefficients). Thus, for the configuration of FIG. 2, i.e., with N=5, there is a total number of 480 unknowns to find.

The optimization procedure uses inputs from P calibration data points. At each point in space three field components are measured. Thus, in total there are 3P equations per frequency (transmitting coil) (where P is several hundred, meaning there are typically over 1000 data points). Because this is overdetermined, e.g., by factor 5 or more, the set of equations (e.g., with 480 unknowns) are solved by optimization.

An initial location of imaginary magnetic source 55 is estimated based on a mechanical drawing, and is iteratively calculated using the disclosed technique. Moreover, the location of each real magnetic source 26 is only approximately known, using the mechanical drawing, e.g., within a given tolerance that is too wide for sufficiently accurate tracking of the distal end of tool 21 inside patient 28, but is accurate enough as an initial condition.

The disclosed iterative calculation can be performed using library functions of a commercial software, such as MATLAB. For example, the exact locations of the magnetic sources can be found using, for example, the f_min_search function of MATLAB, where the solution of the aforementioned set of equations can be done using, for example, the pinv (Moore-Penrose pseudo-inverse) function. A typical cost-function for the error after the M'th iteration is a root-square sum of difference between the M'th iteration calculated magnetic field, $B_{Calc}^M$, and the measured magnetic field, $B_{Meas}$, summed over the sparse grid positions:

$$\text{error}(M) = \sum_{i,j,k} \sqrt{(B_{Calc}^M - B_{Meas})^2} \qquad \text{Eq. 2}$$

where (i, j, k) is a 3D grid position index. Eq. 2 represents three equations, one for each field component measurement.

In an embodiment, using Eq. 1, the processor is configured to provide the magnetic field calibration function as a three-dimensional array of values over a calibrated grid of positions that is denser than the sparse grid used in the measurement.

Figure 4:
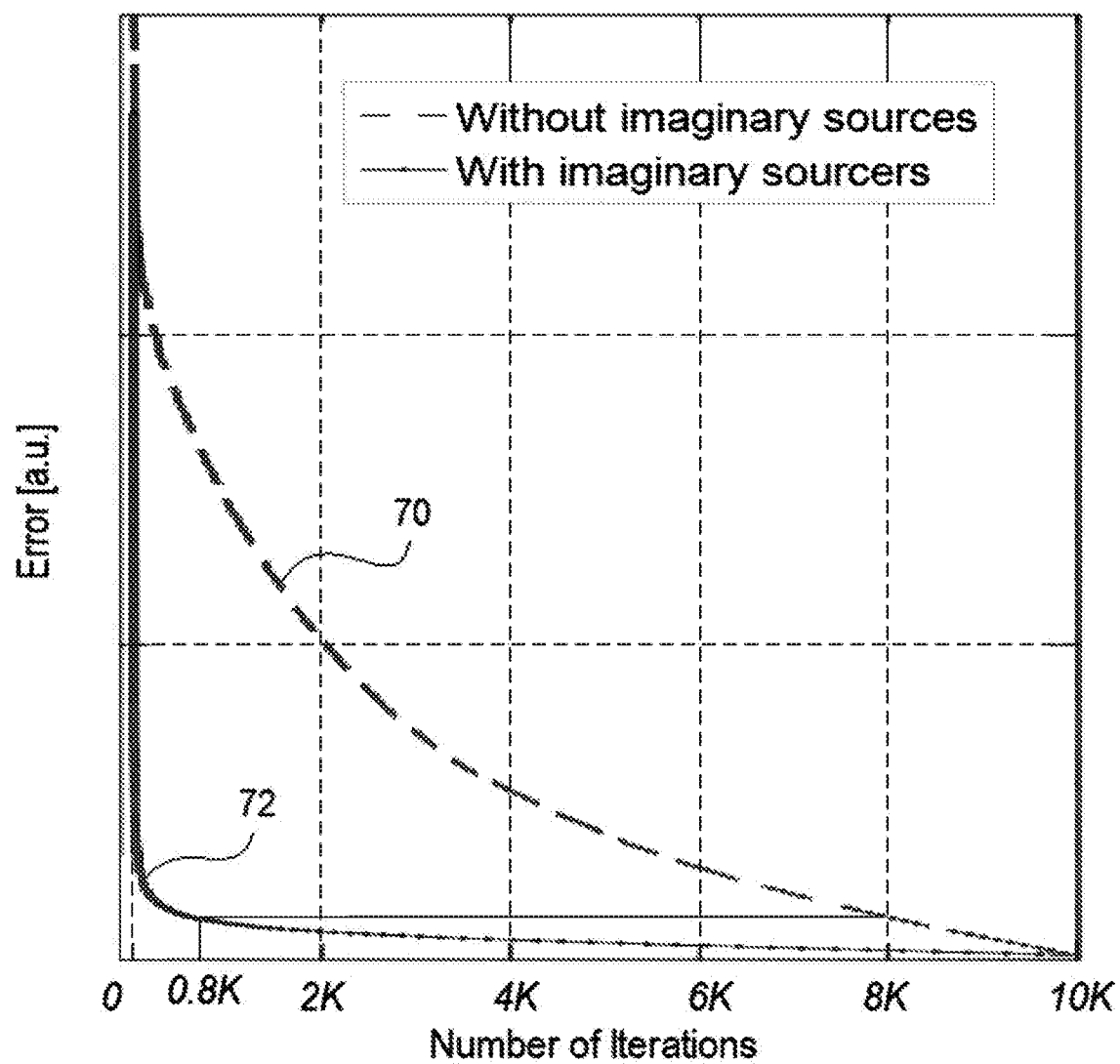
FIG. 4 is a graph plotting the convergence of the iterative calculation locations both without and with the use of imaginary magnetic sources, in accordance with an embodiment of the present invention.

FIG. 4 is a graph plotting the convergence of the iterative calculation locations without the use of imaginary magnetic sources 55 (70) and with the use of imaginary magnetic sources 55 (72), in accordance with another embodiment of the present invention. As seen, by using imaginary magnetic sources and doubling the number of equations to solve at each iteration, the number of iterations until the calibration error falls below a prespecified accepted value fall by a factor larger than ten (e.g., M=8K iteration vs. less than about M≈0.8K iterations, where K is an integer).

Figure 5:
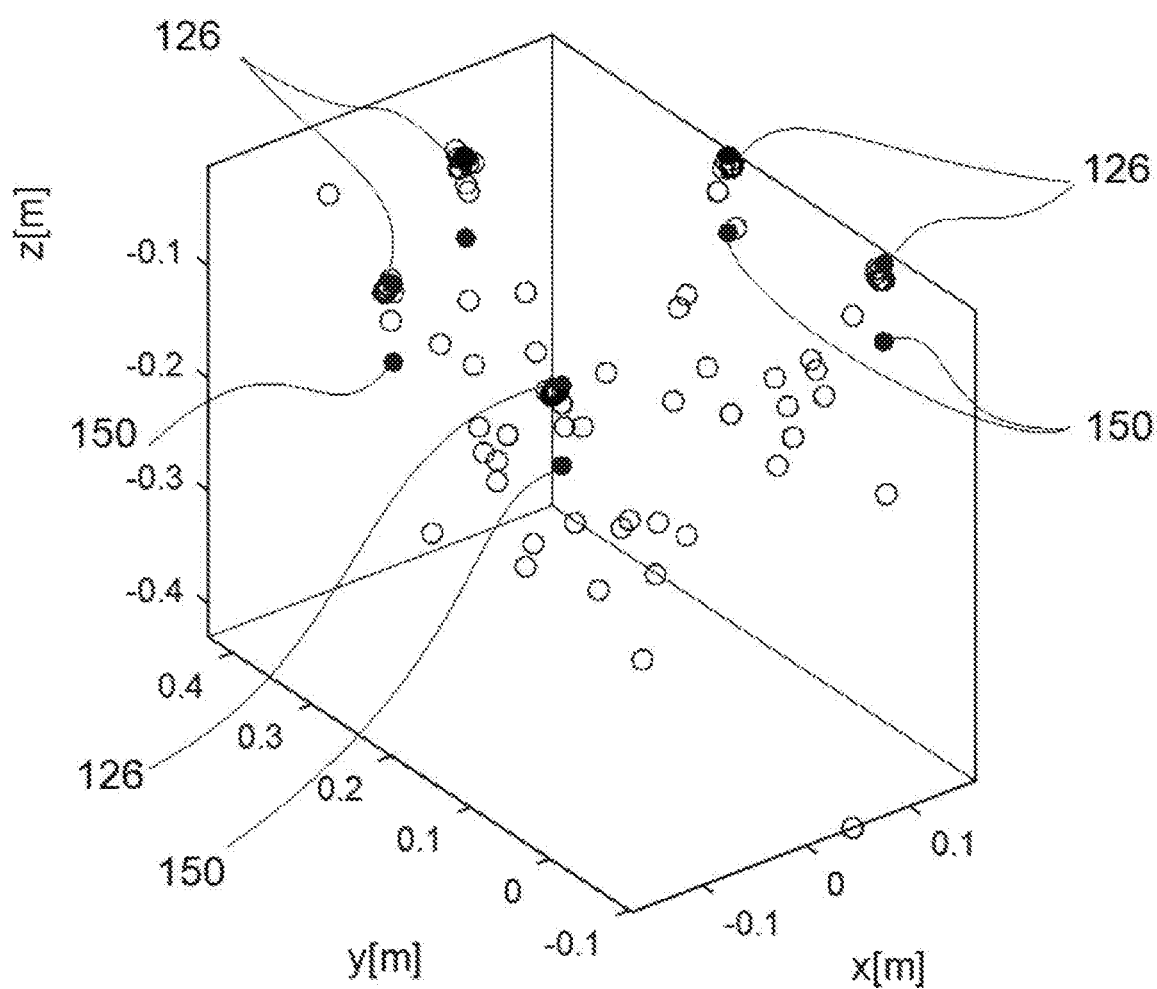
FIG. 5 is plot of the convergence of locations of real and imaginary magnetic sources during an iterative calculation, in accordance with an embodiment of the present invention.

FIG. 5 is plot of the convergence of locations of real and imaginary magnetic sources during an iterative calculation, in accordance with an embodiment of the present invention. The results shown in FIG. 5 are of the disclosed calibration process applied to system 20 of FIG. 1. The open circles are intermediate values of the locations. Full circles 126 are the final locations of real transmitters 26 of system and full circles 150 are the final locations of the respective imaginary sources 55 that are used by the calibration model.

Figure 6:
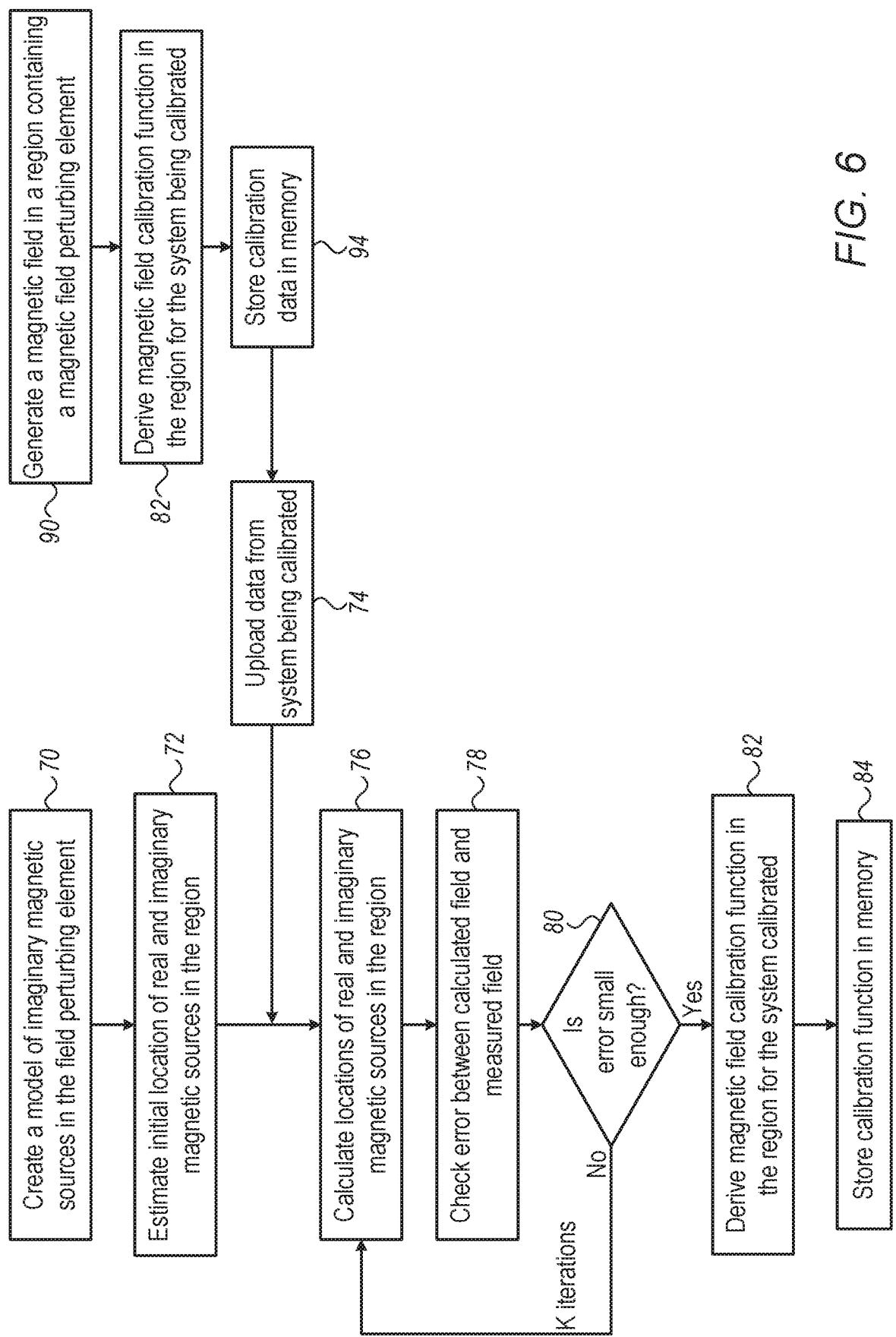
FIG. 6 is flow chart that schematically describes a method of sparse calibration of a magnetic field in the presence of a metal-rich object, in accordance with an embodiment of the present invention.

FIG. 6 is flow chart that schematically describes a method of sparse calibration of a magnetic field in the presence of a metal-rich object, in accordance with another embodiment of the present invention.

The algorithm according to the present embodiment carries out a process that begins with uploading the disclosed model that incorporates imaginary magnetic transmitters in the field-perturbing element to a processor, at a model uploading step 70. Next, at a model initializations step 72, initial locations of the real magnetic sources are inputted to the model in the processor, e.g., by a person who runs the calibration algorithm according to the disclosed model. The initial locations may be taken, for example, from a technical drawing that gives the approximate locations of the real transmitters and dimensions of the perturbing element. The initial locations are typically stored in memory 42.

Typically, the algorithm automatically generates a respective set of location of imaginary magnetic sources, for example, as a mirror reflection of the real sources with respect to an axis of symmetry, as described above.

Steps 70 and 72 are typically common to all systems of a given model and can be done in advance, without the need for hardware-dependent data.

At a system calibration initiation step 74, calibration data from a specific system to be calibrated is uploaded to the processor, e.g., by a person performing the calibration. This data typically comprises uploading a file that stores magnetic field readings, in a form of voltages, over a sparse grid of position in space, where the data in the file is measured independently of the steps concerned with running the calibration model, for example by performing the measurements at a manufacturing floor of the systems, as described below in steps 90-94.

Using the calibration data, the processor iteratively calculates, in steps 76-80, the required calibration function of the specific system.

In a first iteration step 76, the processor calculates locations of the real magnetic sources (26) and imaginary magnetic sources (55) in the region and a respective magnetic field these generate. Next, at an error calculation step 78, the processor calculates, using a cost function as described above, an error between the calculated magnetic field and the measured magnetic field.

At a checking error step 80, the processor compares the error to a prespecified value. If the error is larger than the prespecified value, the processor loops to step 76 to refine the calculation in a next iteration. If the error is smaller than the prespecified value, the processor uses the calculated locations of the real and imaginary magnetic sources to derive a magnetic field calibration function for the system being calibrated, at a calibration step 82. Finally, the processor stores the derived magnetic field calibration function in memory 42, at a calibration storage step 84.

As noted above, the disclosed model is applied to calibrate a specific system. At a preliminary step 90, the system is operated to generate, e.g., by real transmitters 26, a magnetic field in a region, such as region 30 of system 20, that contains the perturbing element (e.g., plate 40).

Next, at a measurement step 92, the magnetic field is measured over multiple positions on a grid in the region, using, for example, a calibration probe fitted with a triaxial magnetic sensor, such as magnetic sensor 34 of ENT tool 21. Finally, the measured calibration data is stored in memory 42, at a data storage step 94, for subsequent use in calibration steps 74-84.

Once the above-described calibration process is completed, processor 41 of system 20 applies the calibration data in accurately tracking the distal end of tool 21 during a medical procedure.

Although the embodiments described herein mainly address ENT medical navigation systems, the methods and systems described herein can also be used in other applications, such as in cardiac, lung, and digestive system procedures as well as in any magnetic tracker with static conductors in the environment.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A calibration method, comprising:
   receiving magnetic field values, which are generated by a plurality of real magnetic transmitters and are measured at multiple positions on a grid in a region containing a magnetic field perturbing element;
   receiving approximate locations of the real magnetic transmitters;
   using the approximate locations, characterizing a respective plurality of imaginary magnetic sources inside the field perturbing element;
   using the measured magnetic field values, the approximate locations, and the characterized imaginary sources, iteratively calculating (i) actual locations of the real and imaginary magnetic sources in the region and (ii) modeled magnetic field values that would result from the real and imaginary magnetic sources at the actual locations; and
   using the calculated locations, and the modeled magnetic field values at the multiple positions on the grid, deriving a magnetic field calibration function for the region.

2. The calibration method according to claim 1, wherein receiving the magnetic field values comprises positioning a probe in the region and measuring the generated magnetic field at the probe over the multiple positions.

3. The calibration method according to claim 1, wherein characterizing the imaginary magnetic sources comprises estimating a location of each of the imaginary magnetic sources inside the perturbing element.

4. The calibration method according to claim 3, wherein the respective plurality of imaginary magnetic field sources comprises, for each real magnetic transmitter in the plurality of real magnetic transmitters, a corresponding imaginary magnetic field source.

5. The calibration method according to claim 4, wherein estimating the location of each of the imaginary magnetic field sources comprises, for each real magnetic transmitter in the plurality of real magnetic transmitters, reflecting that real magnetic transmitter over an axis of symmetry.

6. The calibration method according to claim 1, wherein the magnetic field calibration function is provided as a three-dimensional array of values over a calibrated grid of positions, which is denser than the grid used for measuring the magnetic field values.

7. The calibration method according to claim 1, wherein deriving the magnetic field calibration function comprises modeling the magnetic fields generated by the real and imaginary magnetic sources as linear combinations of spherical harmonic functions, and evaluating the modeled magnetic fields at the actual locations.

8. The calibration method according to claim 1, wherein the field perturbing element is a metal base that provides mechanical support to the plurality of real magnetic field transmitters.

9. An apparatus, comprising:
a memory for storing magnetic field values, which are generated by a plurality of real magnetic transmitters and are measured at multiple positions on a grid in a region containing a magnetic field perturbing element, and for storing approximate locations of the real magnetic transmitters; and
a processor, configured to:
using the approximate locations of the real magnetic transmitters, characterize a respective plurality of imaginary magnetic sources inside the field perturbing element;
using the measured magnetic field values, the approximate locations, and the characterized imaginary sources, iteratively calculate (i) actual locations of the real and imaginary magnetic sources in the region and (ii) modeled magnetic field values that would result from the real and imaginary magnetic sources at the actual locations; and
using the calculated locations, and the modeled magnetic field values at the multiple positions on the grid, derive a magnetic field calibration function for the region.

10. The apparatus according to claim 9, wherein the processor is configured to characterize the imaginary sources by estimating a location of each of the imaginary magnetic sources inside the perturbing element.

11. The apparatus according to claim 10, wherein the respective plurality of imaginary magnetic field sources comprises, for each real magnetic transmitter in the plurality of real magnetic transmitters, a corresponding imaginary magnetic field source.

12. The apparatus according to claim 11, wherein estimating the location of each of the imaginary magnetic field sources comprises, for each real magnetic transmitter in the plurality of real magnetic transmitters, reflecting that real magnetic transmitter over an axis of symmetry.

13. The apparatus according to claim 9, wherein the processor is configured to provide the magnetic field calibration function as a three-dimensional array of values over a calibrated grid of positions, which is denser than the grid used for measuring the magnetic field values.

14. The apparatus according to claim 9, wherein the processor is configured to derive the magnetic field calibration function by modeling the magnetic fields generated by the real and imaginary magnetic sources as linear combinations of spherical harmonic functions, and evaluating the modeled magnetic fields at the actual locations.

* * * * *